(12) United States Patent
Wolkenstoerfer et al.

(10) Patent No.: US 11,311,461 B2
(45) Date of Patent: Apr. 26, 2022

(54) GASTROSTOMY DEVICE WITH PRESSURE MONITORING

(71) Applicants: N.V. NUTRICIA, Zoetermeer (NL); BS MEDICAL TECH INDUSTRY SARL, Niederroedern (FR)

(72) Inventors: Reinhold Wolkenstoerfer, Neunkirchen (DE); Bertrand Basch, Soufflenheim (FR)

(73) Assignee: N.V. Nutricia

( * ) Notice: Subject to any disclaimer, the term of this patent is extended or adjusted under 35 U.S.C. 154(b) by 437 days.

(21) Appl. No.: 16/486,210

(22) PCT Filed: Feb. 16, 2017

(86) PCT No.: PCT/IB2017/000298
§ 371 (c)(1),
(2) Date: Aug. 15, 2019

(87) PCT Pub. No.: WO2018/150217
PCT Pub. Date: Aug. 23, 2018

(65) Prior Publication Data
US 2020/0000683 A1 Jan. 2, 2020

(51) Int. Cl.
*A61J 15/00* (2006.01)
*A61M 25/10* (2013.01)
(Continued)

(52) U.S. Cl.
CPC ....... *A61J 15/0088* (2015.05); *A61J 15/0015* (2013.01); *A61J 15/0049* (2013.01);
(Continued)

(58) Field of Classification Search
CPC ............. A61J 15/0073; A61J 15/0049; A61J 15/0015; A61J 15/0088; A61J 2200/76;
(Continued)

(56) References Cited

U.S. PATENT DOCUMENTS 3,407,817 A * 10/1968 Galleher, Jr. ......... A61M 25/10
604/920
3,780,693 A 12/1973 Parr
(Continued)

FOREIGN PATENT DOCUMENTS

AT           517603 T      8/2011
CN           1950050      4/2007
(Continued)

OTHER PUBLICATIONS

International Search Report and Written Opinion for PCT/IB2017/000298, European Patent Office, dated Feb. 16, 2017.
(Continued)

*Primary Examiner* — Nathan R Price
*Assistant Examiner* — Anh Bui
(74) *Attorney, Agent, or Firm* — Williams Mullen; Thomas F. Bergert

(57) ABSTRACT

A gastrostomy device (100) comprises a gastrostomy tube (200) having a retainer lumen (235) extending between a proximal part and a distal part of the tube (200); and an inflatable retaining element (300) coupled to the tube (200) at the distal part. An interior space of the retaining element (300) is in fluid communication with the retainer lumen (300). The gastrostomy device (100) also comprises an indicator (410) being in fluid communication with the retainer lumen (235) at the proximal part of the tube (200). The indicator (410) is configured for indicating a pressure in the retaining element (300) continuously within a range from a pressure corresponding to an empty retaining element (300) to an optimal pressure for the inflated retaining element (300).

13 Claims, 10 Drawing Sheets

Figure 3:
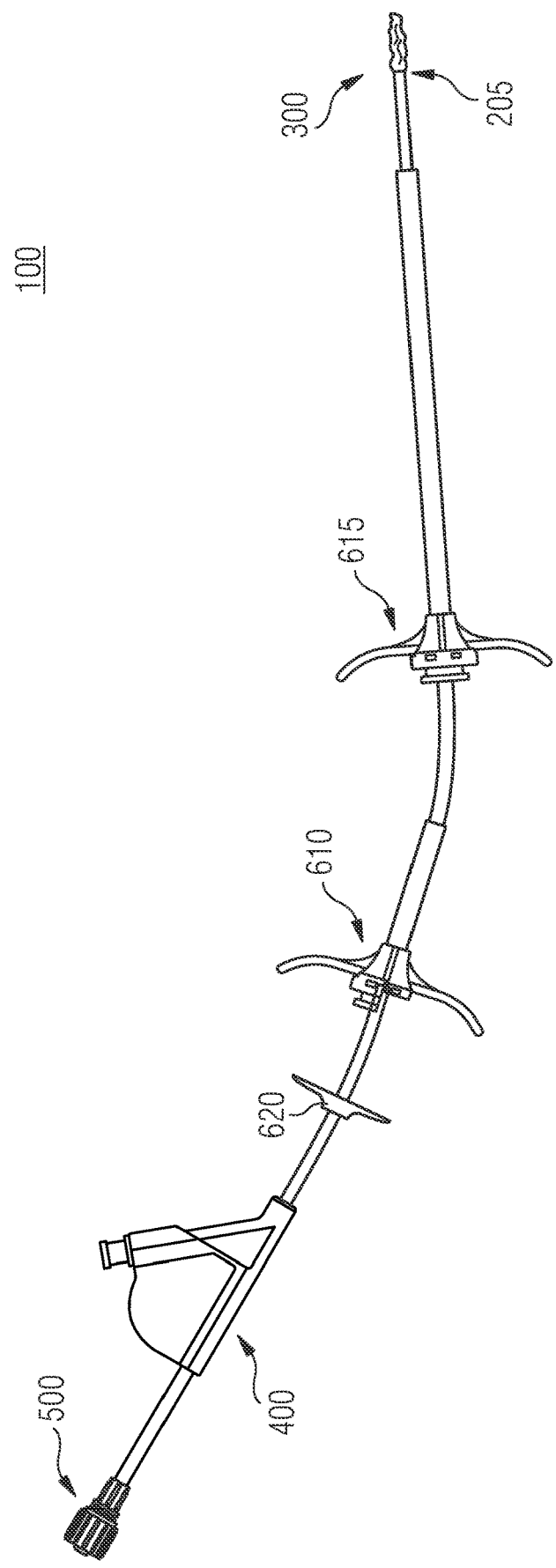

(51) Int. Cl.
*A61M 16/04* (2006.01)
*A61M 25/00* (2006.01)

(52) U.S. Cl.
CPC ........ *A61J 15/0073* (2013.01); *A61M 16/044* (2013.01); *A61M 25/1018* (2013.01); *A61M 25/10187* (2013.11); *A61M 25/10188* (2013.11); *A61J 2200/76* (2013.01); *A61M 2025/0001* (2013.01)

(58) Field of Classification Search
CPC ........ A61M 25/10187; A61M 25/1018; A61M 25/10188; A61M 16/044; A61M 2025/0001
See application file for complete search history.

(56) References Cited

U.S. PATENT DOCUMENTS

| | | | |
|---|---|---|---|
| 5,447,497 A | 9/1995 | Sogard et al. | |
| D418,220 S | 12/1999 | Picha et al. | |
| 6,530,898 B1 | 3/2003 | Nimkar et al. | |
| 8,142,394 B1 | 3/2012 | Rotella et al. | |
| 2002/0157665 A1 | 10/2002 | Igarashi et al. | |
| 2003/0225376 A1* | 12/2003 | Fournie | A61J 15/0042 604/104 |
| 2011/0152762 A1 | 6/2011 | Hershey et al. | |
| 2011/0196341 A1* | 8/2011 | Howell | A61F 5/4408 604/99.04 |
| 2013/0165862 A1 | 6/2013 | Griffith et al. | |
| 2014/0074021 A1* | 3/2014 | Bhagchandani | A61J 15/0065 604/100.02 |

FOREIGN PATENT DOCUMENTS

| | | | |
|---|---|---|---|
| CN | 101903061 | 12/2010 | |
| CN | 102665646 | 9/2012 | |
| CN | 103189034 | 7/2013 | |
| CN | 103269672 | 8/2013 | |
| CN | 203881490 | 10/2014 | |
| CN | 204598864 | 9/2015 | |
| CN | 105944205 | 9/2016 | |
| DE | 4237978 | 2/1994 | |
| DE | 4237978 C1 * | 2/1994 | .......... A61J 15/0003 |

OTHER PUBLICATIONS

Office Action, China National Intellectual Property Administration, CN Patent Application No. 201780086638.3, dated Jul. 23, 2021.
Chinese Patent Office, Chinese Examination Report for Chinese Patent Application No. 201780086637.9, dated Aug. 2, 2021.

* cited by examiner

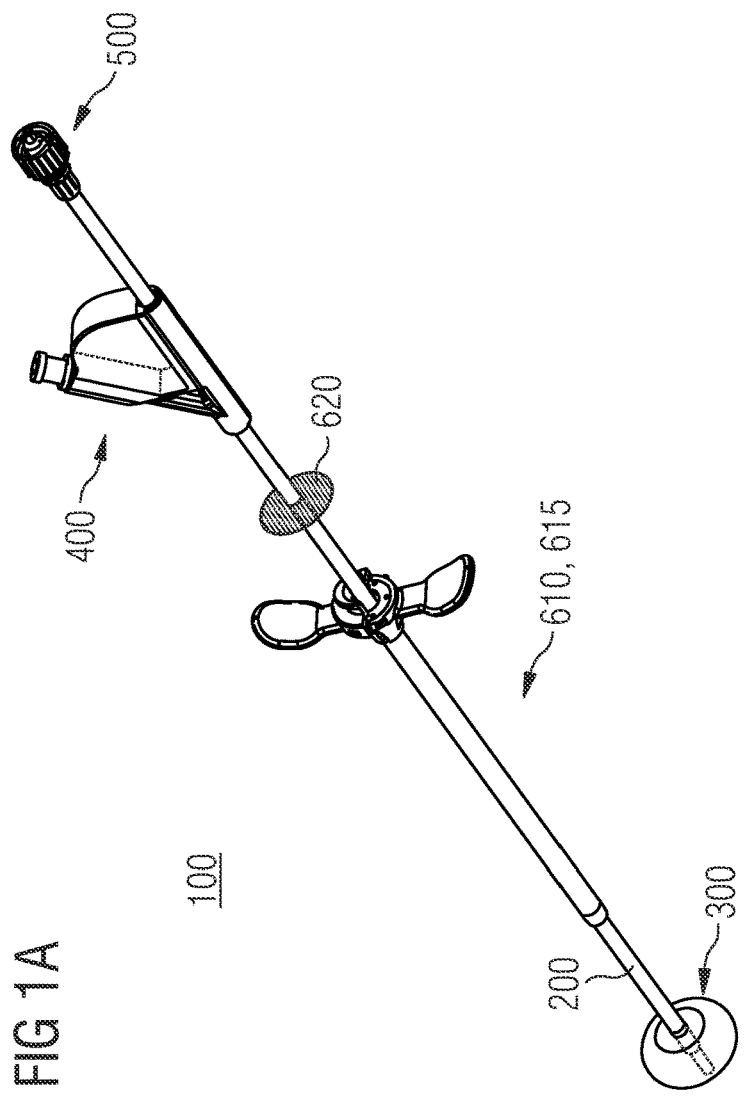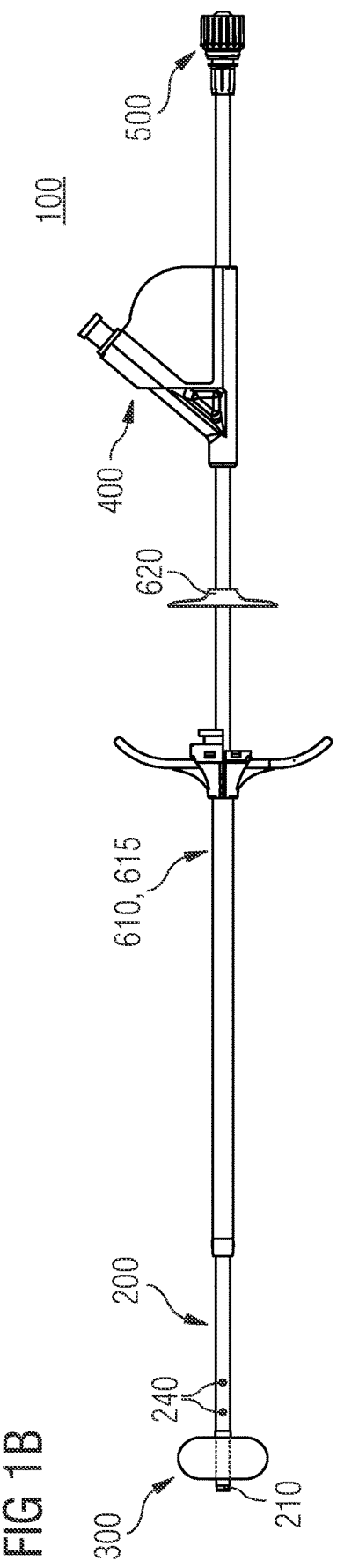

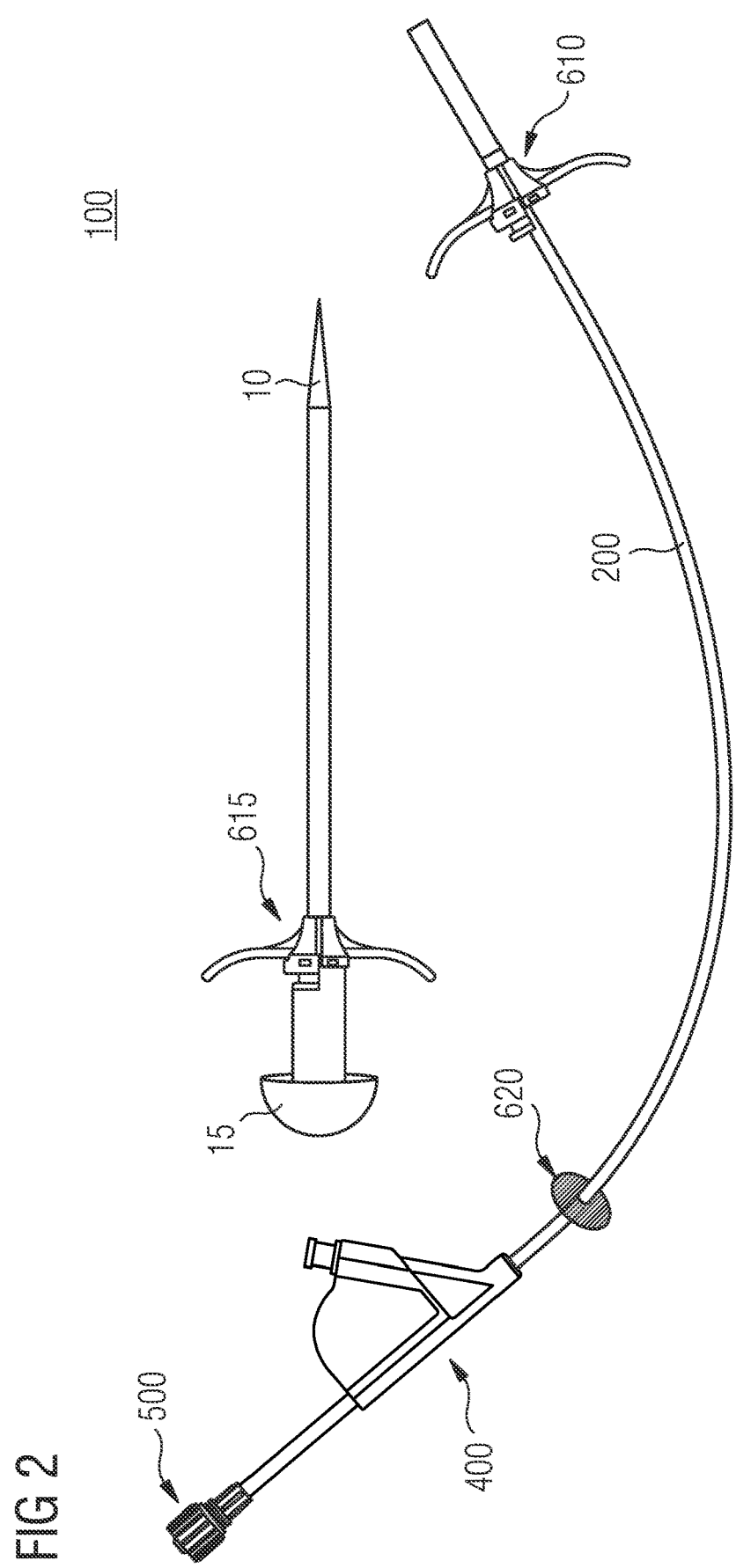

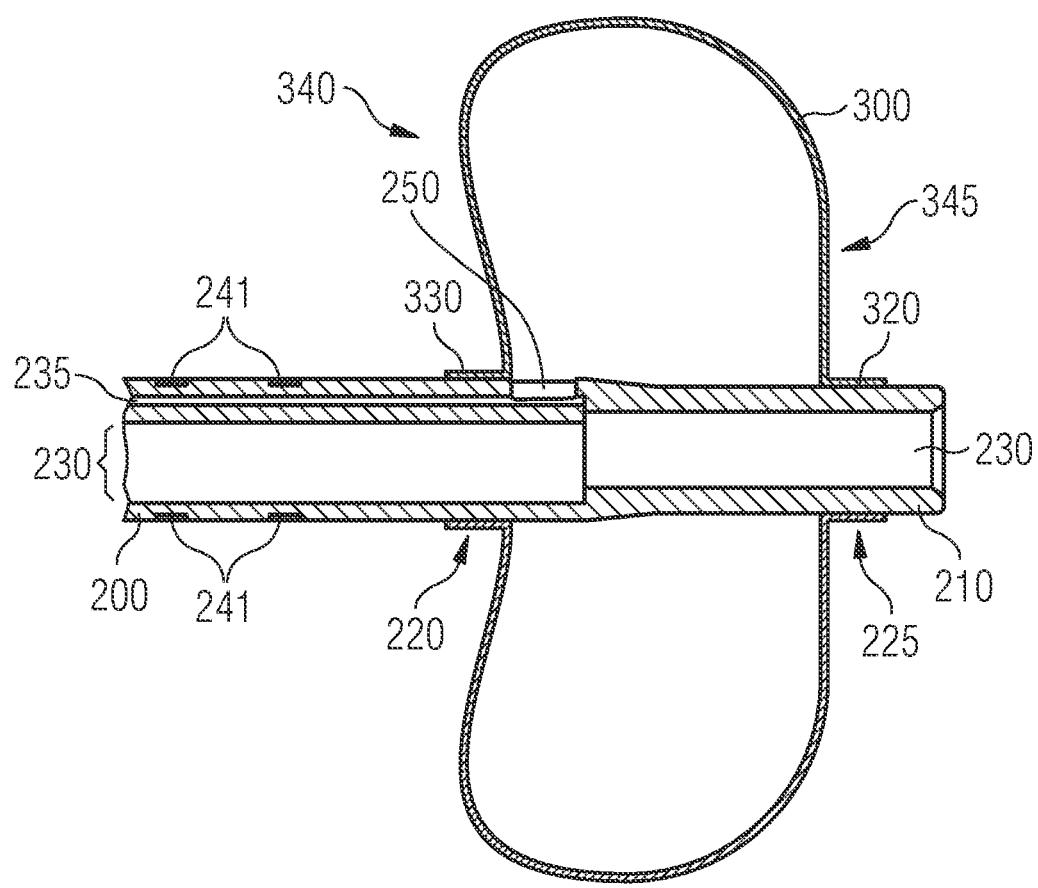

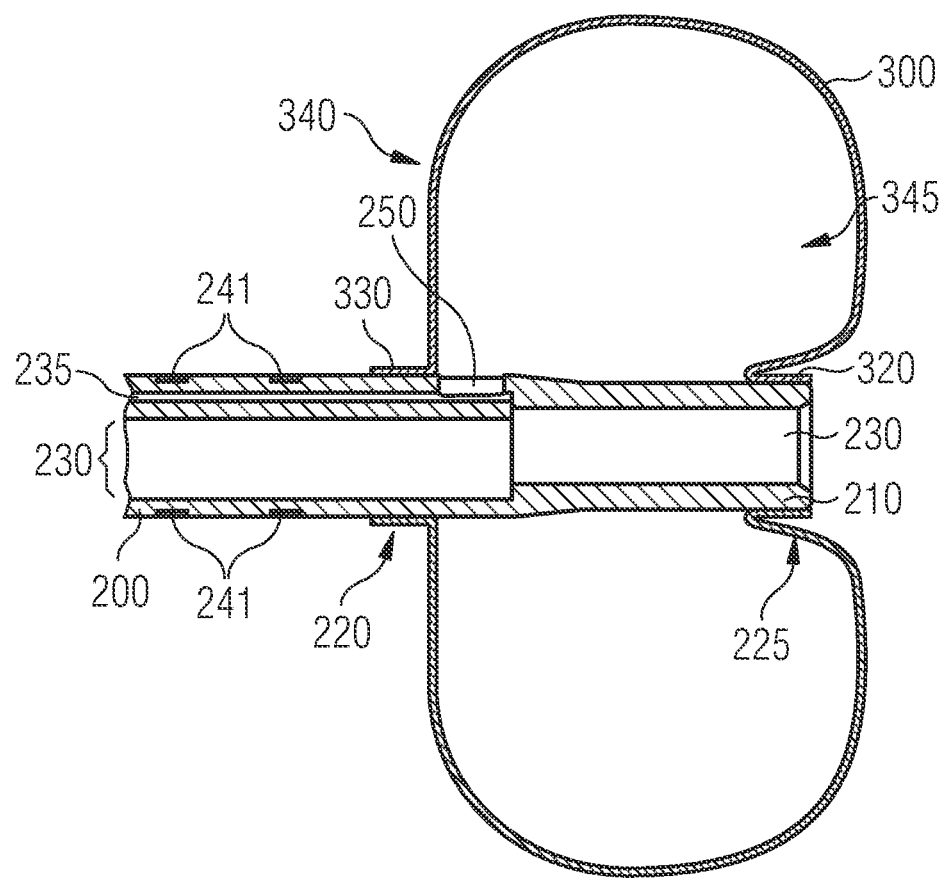

GASTROSTOMY DEVICE WITH PRESSURE MONITORING

CROSS-REFERENCE TO RELATED APPLICATIONS

This application is the U.S. national phase of international application PCT/IB2017/000298, filed on Feb. 16, 2017, which is hereby incorporated herein in its entirety by reference.

The present invention relates to a gastrostomy device, and in particular to a gastrostomy device for percutaneous endoscopic gastrostomy (PEG), which has an indicator indicating a pressure in a retaining element of the gastrostomy device continuously within a range from a pressure corresponding to an empty retaining element to an optimal pressure for an inflated retaining element.

Percutaneous endoscopic gastrostomy is an endoscopic medical procedure in which a tube (PEG tube) is passed into a patient's stomach through the abdominal wall. Typically, such PEG tube serves to provide a means of feeding when oral intake is not adequate or possible. The procedure is an alternative to surgical gastrostomy insertion, and does not require a general anesthetic. PEG tubes may also be extended into the small intestine by passing a jejunal extension tube (PEG-J tube) through the PEG tube and into the jejunum via the pylorus.

In order to place the PEG tube, the abdominal wall and the stomach is punctured with a trocar. A distal end of the PEG tube is then inserted into the stomach. A balloon at the distal end of the PEG tube and an external retainer slidably arranged on the PEG tube hold the PEG tube in place and pull the stomach wall and abdominal wall together. Such balloon as well as the PEG tube are usually made of a silicone material, which allows flexibility for the PEG tube and due to the prolongation of the silicone material an inflatable balloon.

However, the balloon is subject to mechanical influences due to movement of the stomach or the torso of the patient and chemical influences of the stomach fluids. Thus, the balloon may get damaged and will lose pressure, so that the PEG tubes may come out of the stoma. Therefore, some PEG tubes are provided with an indicator that is triggered when an internal pressure of the balloon falls below a certain threshold. For instance, when the pressure within the balloon drops, the indicator provides a visual feedback indicating that the balloon is damaged.

It is an object of the present invention to provide a gastrostomy device having a more reliable indication of the state of a retaining element.

This object is solved by the present invention as defined in independent claim 1. Preferred embodiments are defined by the dependent claims.

In accordance with an aspect of the present disclosure, a gastrostomy device comprises a gastrostomy tube having a retainer lumen extending between a proximal part and a distal part of the tube, and an inflatable retaining element coupled to the tube at the distal part. An interior space of the retaining element can be in fluid communication with the retainer lumen. Furthermore, the gastrostomy device can comprise an indicator being in fluid communication with the retainer lumen at the proximal part of the tube. The indicator can be configured for indicating a pressure in the retaining element continuously within a range from a pressure corresponding to an empty retaining element to an optimal pressure for the inflated retaining element.

The continuous indication of the pressure in the retaining element means that the pressure in the retaining element is steplessly indicated, i.e. the user is provided with a stepless (e.g. proportional) indication of the pressure. Additionally, it can also mean that the pressure is indicated continuously over time, i.e. as long as a pressure above atmospheric level is present in the retaining element, the indicator provides the user with the respective information.

The indicator of the gastrostomy device provides not only more detailed information about the pressure in the retaining element due to a continuous indication of the pressure, but also provides reliable information whether the pressure in the retaining element is in an optimal range or tends towards a pressure corresponding to an empty retaining element. The optimal range of the pressure in the retaining element corresponds to a pressure of a filled retaining element, i.e. the pressure in the retaining element when a fluid filled into the retaining element has fully inflated the retaining element. Usually, medical staff or the patient will have a look at the gastrostomy device and, hence, the indicator regularly, at least once a day. This allows monitoring a development of the pressure within the retaining element.

According to a variant, the indicator can have a scale comprising two sections. A first section can indicate that the pressure in the retaining element corresponds to the empty or insufficiently inflated retaining element, and a second section can indicate that the pressure in the retaining element is in an optimal pressure range for the inflated retaining element. Due to the continuous indication of the pressure in the retaining element, the information derivable from such indicator and scale is much more precise than from conventional indicators, which are triggered by a certain pressure drop, i.e. which provide rather binary information of a filled or empty retaining element.

With respect to a further variant the indicator may be configured for further continuously indicating a pressure in the retaining element corresponding to a range of a pressure-loaded retaining element. Thus, the indicator provides information whether the pressure in the retaining element is above an optimal pressure range, e.g. if the retaining element is subject to a pressure-load, such as a force acting on the retaining element and pulling/pushing it against a wall of a body cavity (e.g. stomach wall). When the pressure of the retaining element is within the pressure-loaded range, the retaining element may be damaged due to an overload pressure.

Furthermore, the scale of the indicator can comprise a third section indicating the pressure-loaded range. An pressure-loaded range is to be understood as a pressure range in which the retaining element may not actually be damaged, but the likelihood for a damage may increase with an increasing pressure inside the retaining element. For instance, the retaining element may still withstand the internal pressure. However, in the course of time other influences on the retaining element may occur, which further increase the pressure (e.g. due to a movement of the stomach wall or due to a movement of the torso of the patient). This additional pressure may then damage the retaining element or other parts of the gastrostomy device.

In addition, during filling the retaining element with a fluid (water, saline solution, glycerin, water-glycerin emulsion, air, etc.), such gastrostomy device allows for monitoring how the retaining element fills up from a rather empty state due to the continuous indication of an increasing pressure. During this filling procedure, which can be conducted with a syringe, it can further be monitored whether enough or too much fluid has been filled into the retaining element, when the indicator arrives and then leaves the second scale section (optimal pressure) and enters into the third scale section (pressure-loaded range).

The indicator (with or without a scale) further provides a direct feedback for the person setting the gastrostomy device into place. In detail, after filling the retaining element with (an optimal amount of) fluid, the gastrostomy device is pulled, so that the stomach wall is brought closer to the abdominal wall. Using a further retaining element, such as a disc-like retaining element, sliding on the gastrostomy tube on an exterior side of the patient the abdominal wall and stomach wall can be pulled together and hold in this position until a stoma is formed. During this process, the (interior) inflatable retaining element is pressed against the stomach wall, whereby the pressure of the fluid inside of the retaining element increases. This pressure increase and, hence, the applied pulling force can be directly derived from the indicator and, in particular, by a pressure indication within the third range (pressure-loaded range) or optionally in the third section of the scale.

Therefore, the indicator of the gastrostomy device provides a plurality of information on a state of the retaining element. Firstly, it is indicated whether the retaining element is empty (first section of the scale). Secondly, the indicator provides information whether the pressure in the retaining element is in an optimal range (second section of the scale). Thirdly, (in the third section of the scale) the indicator provides information whether the retaining element is pulled too hard against the stomach wall, while it can also indicate whether too much fluid is filled into the non-pressure-loaded retaining element. In case the gastrostomy device is secured by an external retaining element in a state where the stomach wall and the abdominal wall are pulled together (by the internal retaining element) the indicator will continuously indicate the pressure in the retaining element according to the third section, since the internal retaining element is pressure-loaded due to the forces acting on the retaining element from the stomach wall. Likewise, the indicator shows whether the retaining element loses pressure (loses fluid) when the gastrostomy device is in place by moving from the third to the second and/or from the second to the first section continuously. This provides for a more reliable indication of the state of the retaining element.

It is to be understood that the indicator of the gastrostomy device is not restricted to two or three sections of the scale. For example, the scale may include four or five sections. For instance, between the first section (empty state) and the second section (optimal pressure range) may be a further section indicating a critically low pressure of the retaining element. This provides information about the retaining element that the pressure is still in the range that the retaining element holds the gastrostomy device in place, but that the retaining element may become loose if the pressure further decreases. Similarly, the third section (pressure-loaded pressure range) may be supplemented with a further section indicating that the pressure in the retaining element becomes critically high. Thus, the user can distinguish between an applied "normal" pulling force and a critically high pulling force or overinflated retaining element.

Referring to a further variant, the indicator may comprise a hollow member being in fluid communication with the retainer lumen at the proximal part of the tube. For instance, an opening in the outer tube skin may be arranged at a longitudinal position of the tube where the indicator is arranged. Fluid running through the retainer lumen can flow through the opening and can enter into the hollow member and vice versa.

According to an exemplary variant, between the opening in the outer tube skin and a proximal end of the tube the retainer lumen can be blocked, e.g., by filling up the retainer lumen. Alternatively, the retainer lumen may be squeezed or pressed together in a manner that the lumen is closed. For example, an adhesive or heat can be employed for closing the retainer lumen. Also alternatively, the tube may be formed differently in this section, i.e., without a retainer lumen. Especially if the retainer lumen is fabricated by extrusion, different sections of the tube can be formed with different cross-sectional shapes having a different number of lumen. Thus, fluid from the retainer lumen flows through the opening and to the hollow member and vice versa.

Furthermore, the hollow member can be configured to receive and hold an amount of the fluid from the retainer lumen in proportion to the pressure in the retaining element. That is, the hollow member allows the fluid to enter an interior hollow space formed by the hollow member. The hollow member is configured for providing with increasing pressure a proportionally increasing resistance against the inflowing fluid.

For example, the hollow member can be configured to have a curved form, when in an empty state, and to straighten, when receiving the fluid. In other words, the fluid received in an interior hollow space of the hollow member inflates the hollow member. This inflating requires a certain pressure, since the hollow member is configured for contracting in a manner squeezing the fluid out of the hollow space. In addition, in an inflated state the hollow member has a substantially longitudinal form, i.e. having a substantially straight form. In a contracted state the hollow member has a curved form, i.e. the hollow member roles itself up to a spiral, circle, ellipse, etc. or part thereof. The hollow member may be made of PUR (or PU) having a hose-like form, where an end opposite to an end from which fluid from the retainer lumen enters the hollow member is closed, e.g. by welding or adhering.

The hollow member may further have a visual indicator visible from an outside of the indicator, in particular from an outside of a casing of the indicator. For example, at least a part of the hollow member, such as an end of the hollow member opposite to an end from which fluid from the retainer lumen enters the hollow member, may have a different color, material, form, etc. The entire hollow member may form the visual indicator or at least that part of the hollow member that will be visible from an outside (of a casing) of the indicator over all pressure ranges indicated by the hollow member. Alternatively or additionally, a separate element is attached to the hollow member as the visual indicator.

Alternatively, the indicator can comprise a piston movably disposed inside the hollow member and a return member configured for returning the piston to a neutral position inside the hollow member. An outer surface of the piston sealingly fits to an inner surface of the hollow member, so that the piston moves due to a pressure change inside the retainer lumen. The sealingly fitting outer surface of the piston thereby prevents liquid from flowing around the piston to a distal end of the hollow member, i.e. an end opposite to an end from which fluid from the retainer lumen enters the hollow member.

The neutral position of the piston can correspond to a pressure in the retainer lumen (or actually the absence of a pressure) when the inflatable retaining element is in an empty state. The return member, therefore, is configured for moving the piston to the neutral position when substantially no pressure acts against the piston towards the distal end of the hollow member. Furthermore, the return member provides an increasing resistance against the fluid pressure acting on the piston, so that the piston moves inside the hollow member depending on the pressure of the fluid acting on the piston.

The indicator may further have a visual indicator visible from an outside of the indicator. The visual indicator is fixedly coupled to the piston or is integrally formed with the piston. For instance, the hollow member can be transparent, so that a visual indicator coupled to or provided on the piston is visible from the outside of the indicator. The visual indicator can also be implemented by providing a part of the piston in a different color, a different material, etc. Alternatively, the visual indicator may be arranged outside of the hollow member and is coupled to the piston magnetically. For example, the piston or the visual indicator can be provided with a magnet, while the other one of the piston and the visual indicator is provided with a material attracted to the magnetic field or a second magnet. When the piston is moved due to a pressure change, the visual indicator moves correspondingly due to the magnetic coupling of the piston and the visual indicator.

In any case, a visual indicator may be visible from an outside of the indicator in an area where the scale of the indicator is provided. For instance, the indicator (or a casing thereof) may be provided with a transparent window adjacent to the scale and, in particular, adjacent to all sections of the scale. The visual indicator or simply the hollow member may be visible through that window. The visual indicator and the scale can be arranged relatively to each other, so that the visual indicator moves along or within the sections of the scale. Furthermore, the hollow member or the piston may be configured for moving the visual indicator from one end of the first section to an opposite end of the last section of the scale. If the entire hollow member forms the visual indicator the relative position of the hollow member and the scale can easily be achieved, since the hollow member moves on a circular or spiral path and a part of the hollow member is always visible from an outside, such as through a curved, circular, spiral window.

Alternatively or additionally, the indicator can comprise an electrical or electronic indicator capable of providing an audible or visual signal. For example, the indicator may include one or more piezoelectric elements activated by the hollow member depending on (a) certain pressure level(s) of the pressure in the retaining element, i.e. depending on (a) position(s) of the hollow member or the piston. A plurality of piezoelectric elements can be arranged corresponding to each section of the scale, so that continues indication of the pressure in the retaining element can be achieved. This provides for another way of indicating to a user that the pressure in the retaining element has reached or is within a certain range.

The electric current produced by such piezoelectric element(s) can then be used by an audio component outputting an audible signal and/or a lighting component or display outputting a visible signal. A lighting component can be one or more light emitting diodes emitting a light according to the pressure level in the retaining element. The display can be any form of a display component (e.g. liquid crystal display panel) visually indicating of value of the pressure in the retaining element. The electric current can also be employed to send a signal (wireless or via a wired connection) to a monitoring system, e.g. a monitoring system of the hospital, and/or a nurse call system. This allows (additional) remote monitoring of the pressure in the retaining element of a certain patient or a plurality of patients.

According to another variant, the gastrostomy device further comprises a fitting configured for detachably connecting the hollow member to a lumen being in fluid communication with the retainer lumen. The hollow member can have a corresponding fitting for connecting the hollow member and bringing it in fluid communication with the retainer lumen. For instance, the fitting can be a Luer-connection, Luer-Lock-connection or an ENFit-connection (according to ISO norm 80369-3). This detachable connection of the hollow member allows the use of any gastrostomy device (e.g. legacy gastrostomy device), to which the hollow member can simply be attached for an indication of the pressure within the retaining element. Such gastrostomy devices usually include a corresponding fitting, via which the retaining element is inflated. This available fitting can be used to attach the hollow member for pressure monitoring. In addition, the hollow member and the indicator may form a unit that can be connected to the retainer lumen of the (legacy) gastrostomy device via the fitting. This allows detachably connecting the indicator including a visual indicator (of the hollow member or simply the hollow member) to the (legacy) gastrostomy device for pressure monitoring of the retaining element.

In accordance with a further variant, the gastrostomy device comprises a pull handle connected to the tube in a force-fitting manner, wherein the pull handle is configured for pulling the tube. The pull handle can be connected to the tube by welding, adhesive bonding and/or fixing means based on a frictional force applied on the outer skin of the tube. The pull handle can further be formed asymmetrically or symmetrically around the tube. In any case it is configured to be gripped by one or more fingers of a user to pull the tube and, hence, the inflated retaining element, so that the (inflated) retaining element abuts against the stomach wall.

Referring to another variant, the gastrostomy device can comprise a connector configured for receiving a filling means and being in fluid communication with the retainer lumen of the tube at a proximal part. The connector allows filling a fluid through the retainer lumen into the retaining element. For example, the connector may be configured for receiving a syringe or other filling means filled with a fluid, such as water, a saline solution, air or other gas. An operator can fill the fluid from the filling means through the connector into the retainer lumen and further into the retaining element.

The connector may be connected to the same opening in the outer skin of the tube into the retainer lumen, to which the hollow member is connected to. This allows forming the indicator and the connector as an integrated component of the gastrostomy device, which renders the gastrostomy device less complex. In addition, the indicator will react directly on any pressure change due to a reduction of other influences, for example due to a prolongation of any lumen of the gastrostomy device.

Alternatively, the connector can be provided at a different proximal part of the tube that is spaced apart from the proximal part of the tube, where the indicator is arranged. This requires a second opening in the outer skin of the tube into the retainer lumen, so that the connector is in fluid communication with the retainer lumen. This arrangement of the connector avoids blocking the view to the indicator when operating the filling means coupled to the connector.

The connector can include a valve configured for blocking and deblocking the fluid communication to the retainer lumen. For example, the valve may be disposed in or close to the connector, such that the filling means when inserted into the connector opens the valve. Similarly, when the filling means are removed from the connector, the valve closes, for example, by return means, such as a spring or other force loaded component acting on the valve.

According to an exemplary variant, the connector can be formed integrally with the pull handle. This is particularly advantageous, if the connector and the hollow member of the indicator share the same opening in the outer skin of the tube into the retainer lumen. It allows forming the connector and pull handle as a compact integrated component of the gastrostomy device. Furthermore, the hollow member may be in fluid communication with a part of the connector that itself is in fluid communication with the retainer lumen. For example, between the valve of the connector and the opening in the outer skin of the tube into the retainer lumen a connector lumen can be arranged. A further lumen branching off from the connector lumen can lead to or be the hollow member.

In accordance with an implementation variant, the connector forms part of a first branch of a Y-connector. For instance, a connector lumen is in fluid communication with the retainer lumen via an opening in the outer skin of the tube, where the connector lumen forms a particular angle with the tube, such as an angle of 30° to 60°, or 40° to 50°, preferably 45°. At an end of this first branch facing away from the tube the connector is disposed.

According to a further implementation variant, a second branch of the Y-connector includes a fitting. Such fitting is configured for receiving another fitting, such as an adapter, allowing the connection of a further lumen to the second branch of the Y-connector. For example, the fitting may be configured to provide a Luer connection, Luer-Lock connection, an ENFit connection (according to ISO norm 80369-3), or other standardized connecting means. The fitting of the second branch is in fluid communication with another lumen of the tube, such as a gastric lumen being different from the retainer lumen. This gastric lumen allows the provision of a fluid into the stomach of the patient. Alternatively or additionally, the gastric lumen provides for guiding another longitudinal tool into the stomach of the patient.

Alternatively to the above variant, the tube can pass through (the second branch of) the Y-connector and extends from the second branch of the Y-connector. This allows the connection of the tube at a distal end spaced apart from the Y-connector, so that an operator is not hindered by any components coupled to the first branch of the Y-connector.

Furthermore, the gastric lumen extends at least between the proximal part and the distal part of the tube, wherein the gastric lumen is configured to let nutrition and/or medication and/or gas pass through. The gastric lumen can extend to a distal end tip of the tube. Thus, the gastric lumen extends from a fitting (e.g. at a Y-connector) to the distal end tip of the tube.

The gastric lumen has a cross-section that allows nutrition, medication and/or gas pass through. For example, the cross-sectional shape of the gastric lumen may substantially correspond to a circle. Only in an area of the cross-section of the tube, where the retainer lumen is arranged, the cross-sectional shape of the gastric lumen has an indentation. Since no niches are formed in the cross-sectional shape of the gastric lumen, clogging within the gastric lumen can be avoided.

According to a further variant, the retainer lumen has a cross-section forming an ellipse, wherein a minor axis of the ellipse aligns with a radially direction of a cross-section of the tube. Thus, the retainer lumen can be fitted into an outer skin of the tube in a space-saving manner. Furthermore, the retainer lumen of such cross-section and arrangement provides for greater curvatures of the cross-section of the gastric lumen, so that the cross-section of the gastric lumen does not have niches.

In addition, such retainer lumen, where facing the exterior side of the tube, extends wider in a circumferential direction than compared to a circular cross-section or different arrangement of the retainer lumen in the tube. This facilitates the creation of an opening into the retainer lumen. In addition, the opening facilitates fluid communication between the retainer lumen and a lumen leading to the connector and/or the hollow member, since it can be wider than with a circular cross-section of the retainer lumen.

Furthermore, since the retainer lumen has to transport water, a (saline) solution, glycerin, water-glycerin emulsion, air or a similar gas, the cross-sectional size of the retainer lumen can be smaller than that of the gastric lumen which transports more viscous fluids. For example, the cross-sectional area of the retainer lumen can be between 3% and 10% of a cross-sectional area of the gastric lumen.

In yet another variant the tube can comprise indication elements disposed circumferentially and/or along a longitudinal direction of the tube. In a circumferential direction, the indication elements can be uniformly distributed, such as three indication elements every 120°. At at least some of the indication elements can be spaced apart from each other in the longitudinal direction of the tube by a predetermined distance. For example, at least some of the indication elements can be provided at equal intervals, such as 0.5 cm, 1 cm, 1.5 cm, or a similar distance providing a graduation of an insertion length of the gastrostomy device.

At least some of such indication elements can be visible from the outside of the tube. For instance, the indication elements can be printed onto an exterior surface of the tube. Alternatively or additionally, at least some of the indication elements can be integrated into a wall of the tube. An exemplary indication element can be integrated into the wall of the tube during fabrication of the tube. For instance, when the tube is fabricated by extrusion, a different material, colored material (same as the remaining extruded material), ink, etc. can be introduced into the tube wall. An indication element fully integrated into the tube wall reduces the risk of a burst of the tube. In particular, if the material of the tube does not fully coat an outer surface of the indication element, a predetermined breaking point may be formed where the material of the tube may break, e.g. due to an internal pressure inside the tube. Likewise, the indication element being of a different material than the tube may uncouple from the material of the tube, thereby damaging the tube.

Furthermore, also alternatively or additionally, each indication element may include a contrast agent. Thus, at least some of the indication elements can form markers. This allows for detecting the indication elements (markers) and, hence, the tube under x-ray or similar technique. Such markers can be provided continuously in a longitudinal direction of the tube. This allows confirming the position of the tube inside the patient's body.

The gastrostomy device can be employed when forming a stoma, i.e. immediately after piercing through the abdominal wall and stomach wall. Such gastrostomy device usually requires a longer gastrostomy tube for a convenient handling. For example, the gastrostomy tube is provided with a protection sheath and has to be inserted through an access sheath. Furthermore, the gastrostomy device can also be employed after a stoma has been formed and enteral feeding is continued. Such gastrostomy device, also referred to as a replacement product/tube, G-Tube or Button, requires a shorter gastrostomy tube, since it can be pushed directly through the stoma without any sheaths.

In accordance with another aspect of the present disclosure, a gastrostomy kit comprises a trocar, one or more tear sheaths, and a gastrostomy device including a gastrostomy tube, inflatable retaining element and indicator.

It is to be understood that the described aspects and variants do not restrict the present disclosure to the exemplary aspects and variants. Rather any combination of such aspects and variants shall fall under the scope of the present disclosure.

Figure 4A:
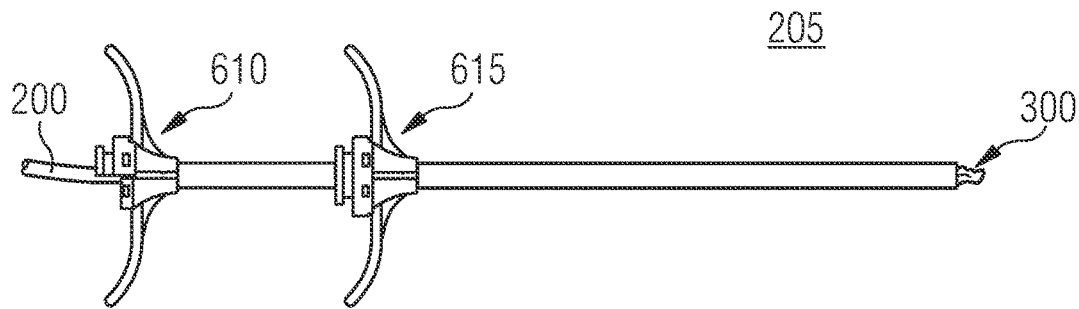
Figure 4B:
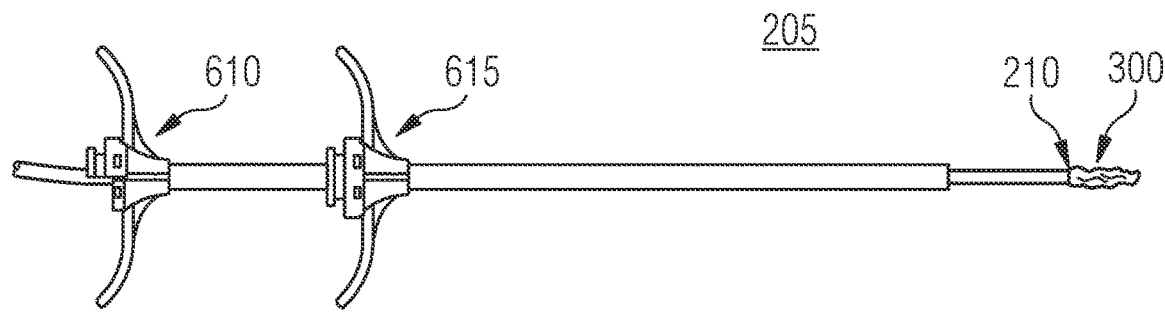
Figure 4C:
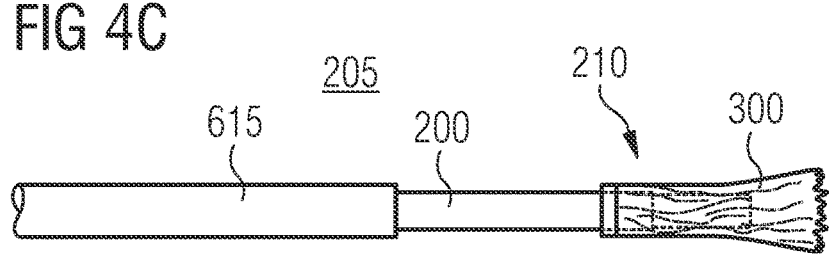
Figure 4D:
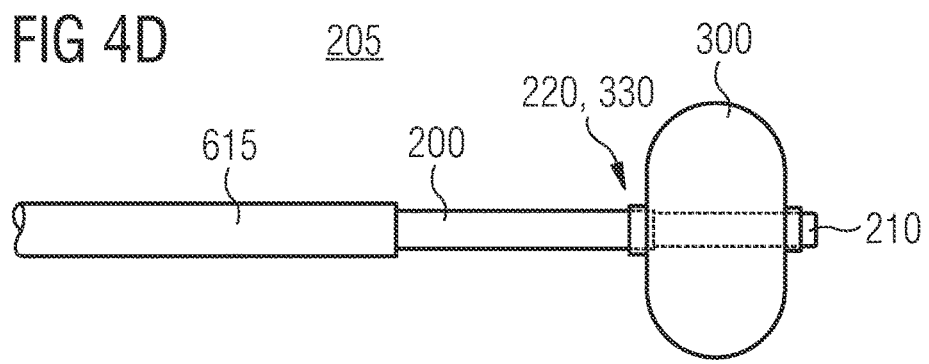
Figure 5A:
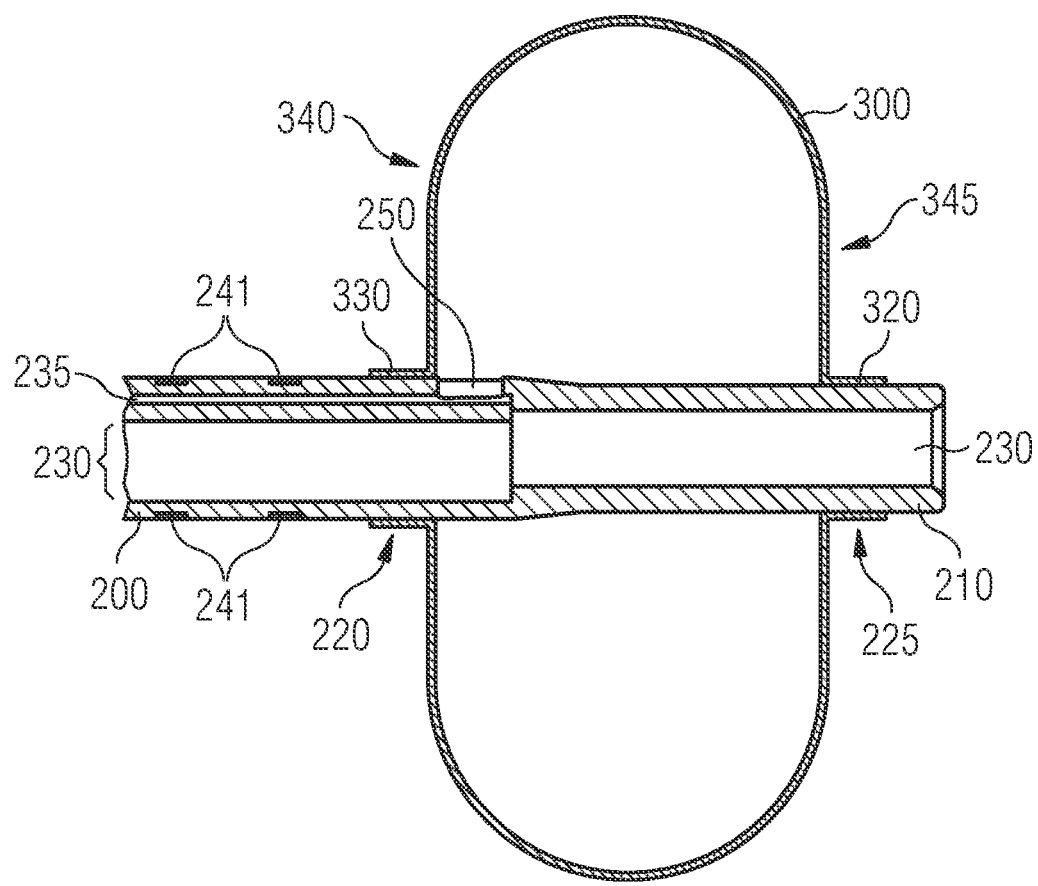
Figure 6A:
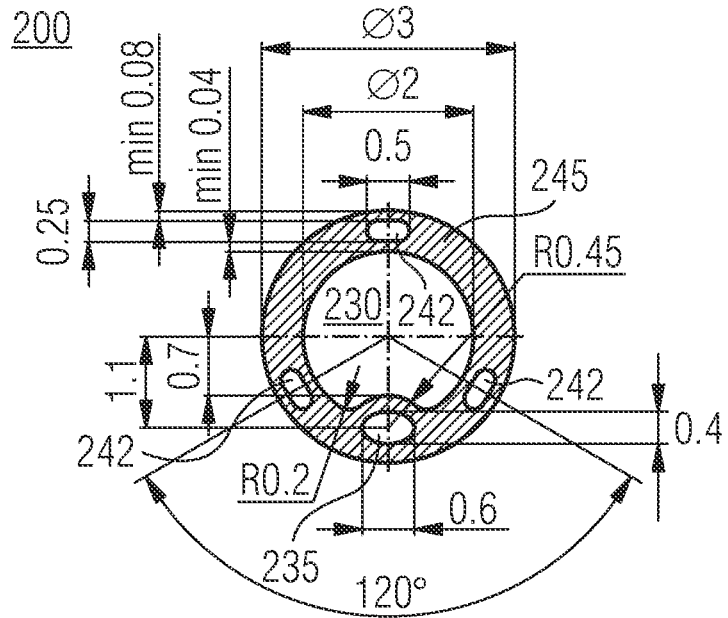
Figure 6B:
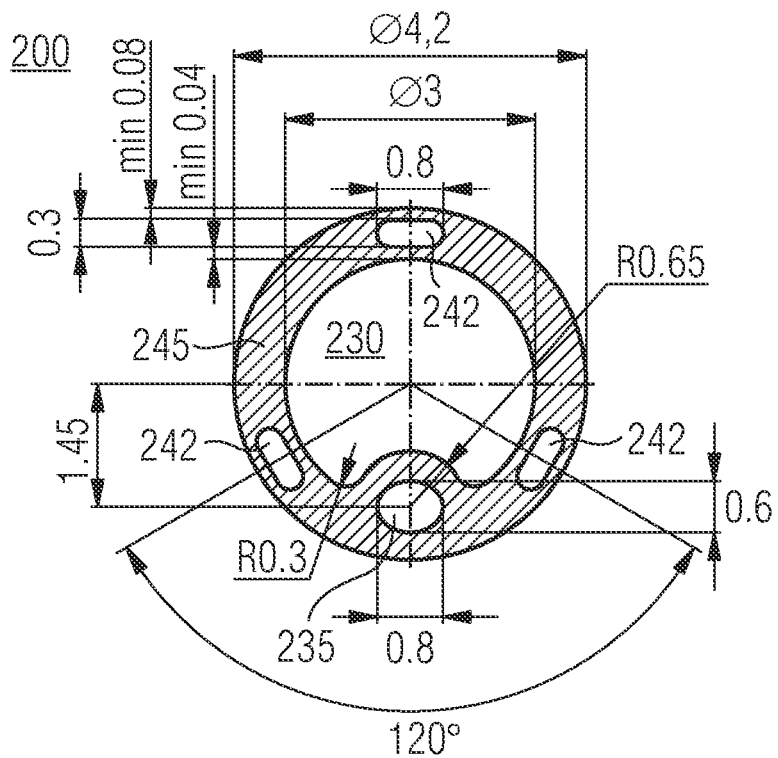
Figure 7A:
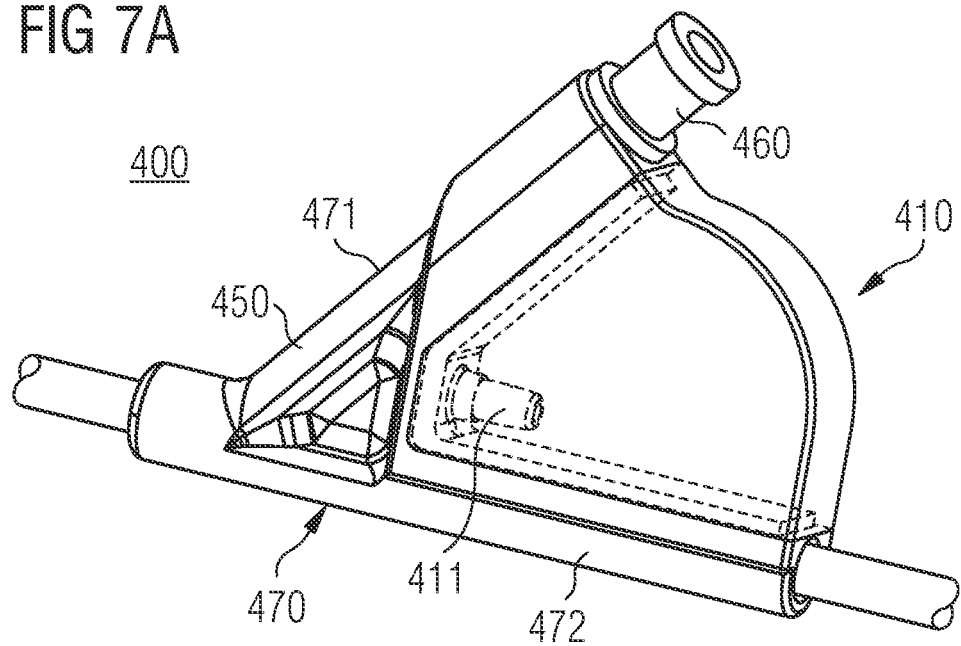
Figure 7B:
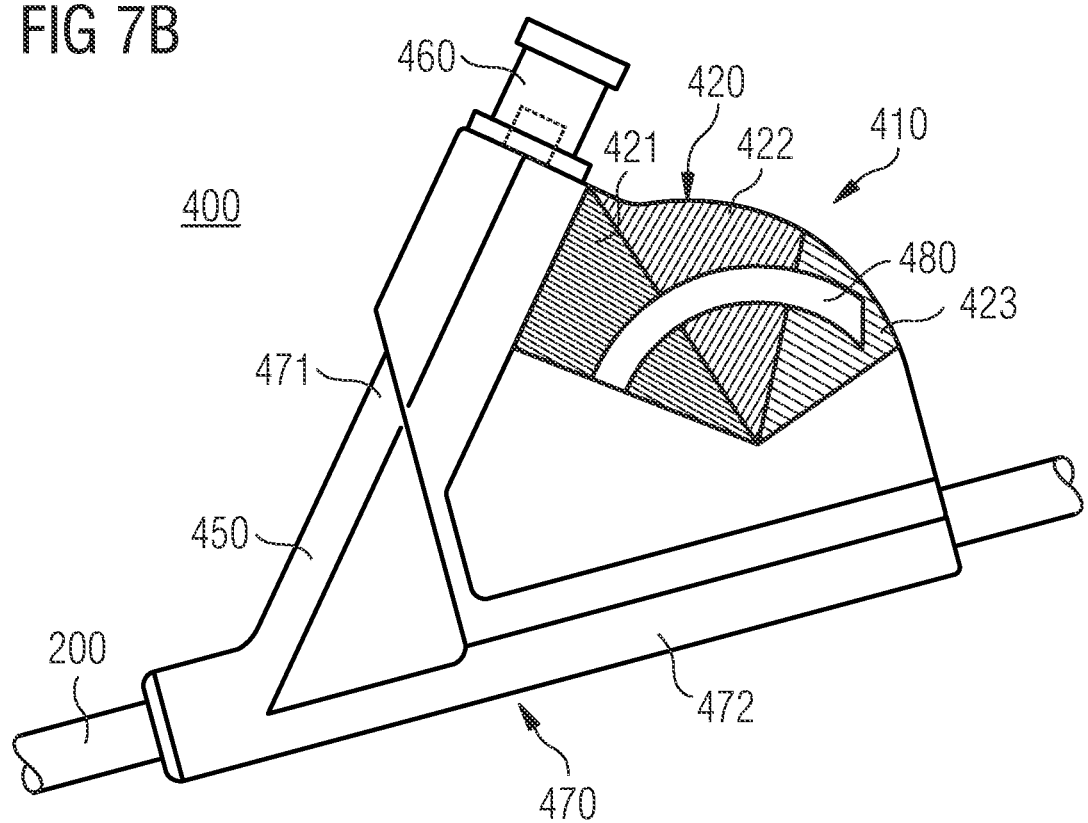
Figure 8A:
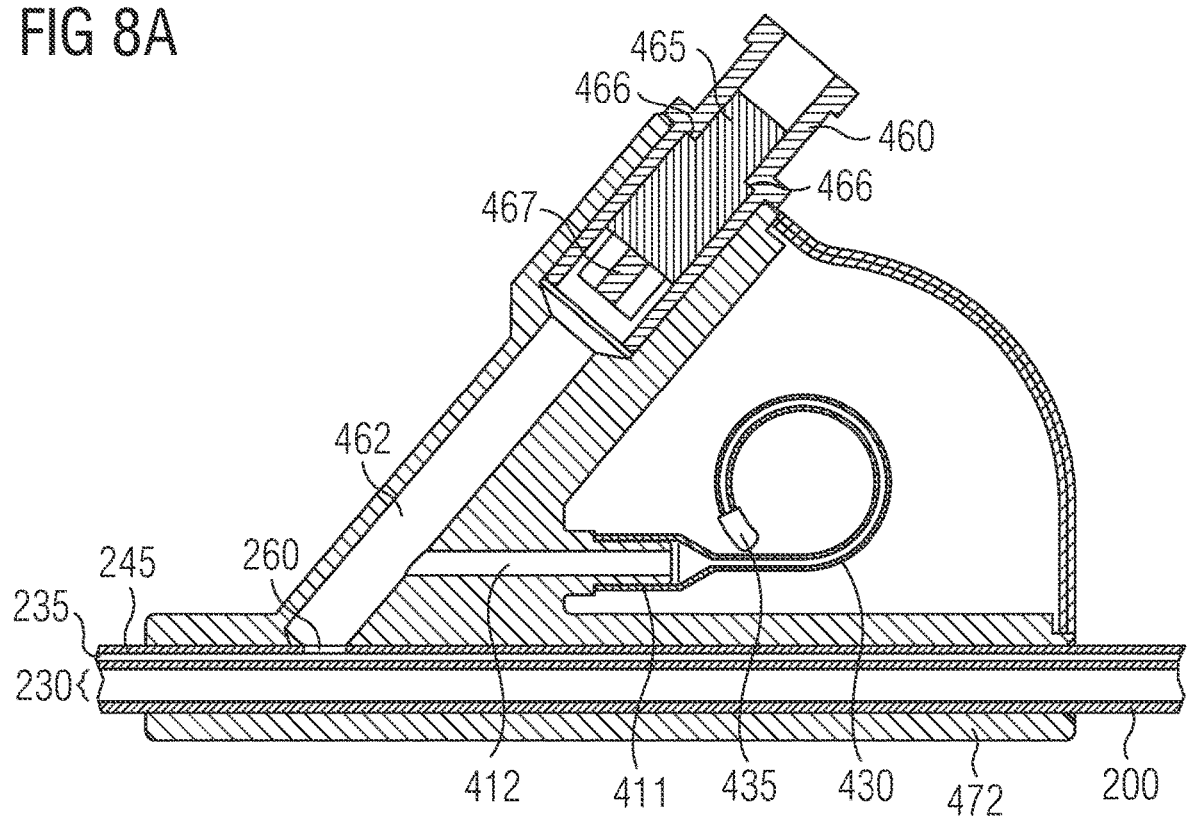
Figure 8B:
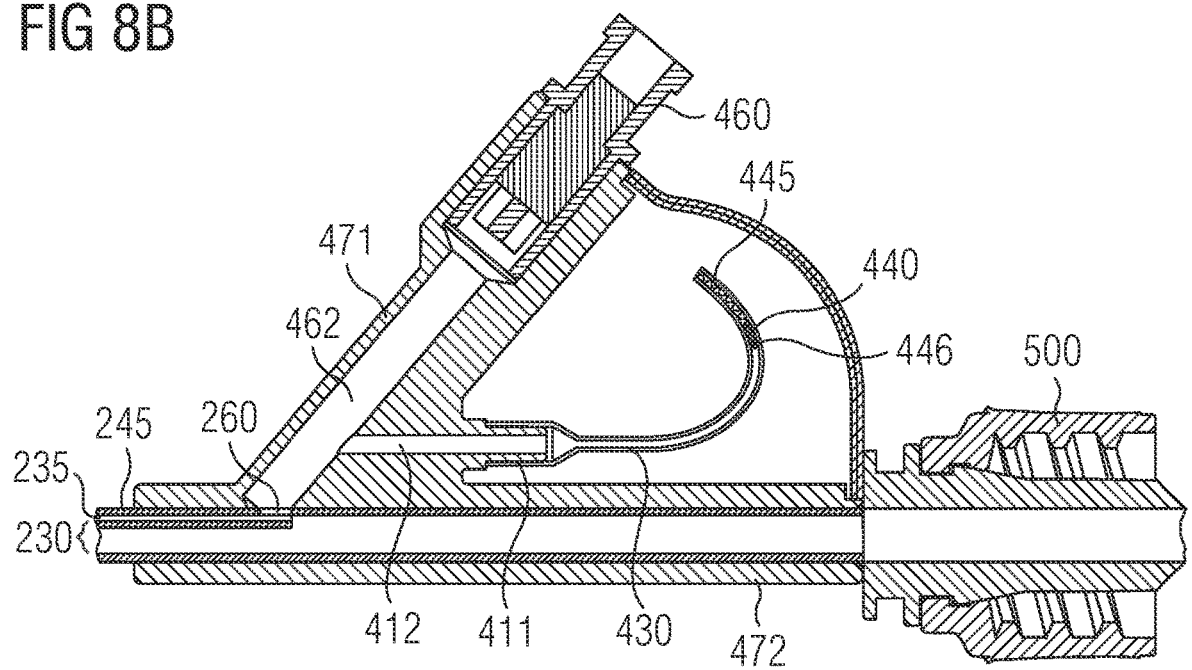

Preferred examples of a gastrostomy device are described in greater detail with reference to the attached schematic drawings in the following, wherein FIGS. 1A and 1B show a perspective view and a side view of a gastrostomy device, respectively, including an access sheath sheathing a portion of the gastrostomy device, FIG. 2 shows a side view of a gastrostomy device including a protection sheath sheathing a portion of the gastrostomy device and a trocar sheathed by an access sheath, FIG. 3 shows a side view of a gastrostomy device including a protection sheath and an access sheath each sheathing a respective portion of the gastrostomy device, FIGS. 4A to 4D show a distal end of a gastrostomy device in more detail, and in particular show a retaining element at a distal end of a gastrostomy device sheathed by a protection sheath and an access sheath at different states, FIGS. 5A to 5C show a sectional side view of respective variance of a retaining element in an inflated state at a distal end of a gastrostomy device, FIGS. 6A and 6B show a cross-section of gastrostomy tubes of exemplary sizes CH10 and CH14, respectively, FIGS. 7A and 7B show a perspective view and a side view of a connector arrangement provided at a proximal part of the tube, respectively, and FIGS. 8A and 8B show sectional side views of two exemplary connector arrangements.

The following detailed description of the schematic drawings focuses on the illustrated implementation variants of a gastrostomy device. The present disclosure is not limited to the above and below described and illustrated gastrostomy devices, but includes combinations of the described variants and implementation details of these gastrostomy devices.

FIGS. 1A and 1B show a perspective view and a side view of a gastrostomy device 100, respectively. The gastrostomy device 100 includes a gastrostomy tube 200, which forms the main component of the gastrostomy device 100 in a longitudinal direction thereof. At or near the distal end of the gastrostomy tube 200 is an inflatable retaining element 300 coupled to the tube 200. The distal end of the tube 200 and the retaining element 300 will be inserted into a body cavity of a patient, such as the stomach, when the retaining element 300 is in an empty state. Nevertheless, for a better understanding of the overall structure of the gastrostomy device 100 FIGS. 1A and 1B illustrates the gastrostomy device 100 with an inflated retaining element 300.

In order to facilitate inflation of the retaining element 300, the tube 200 comprises a first lumen, i.e. a retainer lumen, extending in a longitudinal direction of the tube 200. The retainer lumen is in fluid communication with an interior space of the retaining element 300. A connector arrangement 400 is provided at a proximal part of the tube 200. A connector of the connector arrangement 400 is in fluid communication with the retainer lumen and provides for coupling of filling means thereto, so that a fluid can be filled from the filling means through the retainer lumen into the interior space of the retaining element 300. Thereby the retaining element 300 is inflated (filled with the fluid) and achieves a form exemplarily shown in FIGS. 1A and 1B. The fluid may be water, a saline solution, glycerin, water-glycerin emulsion, air or other gas.

When inflated, the retaining element 300 retains the gastrostomy device 100 in the body cavity of the patient, such as the stomach. A user can pull the gastrostomy device 100, so that the retaining element 300 abuts against an interior wall of the body cavity, such as the stomach wall. For example, the user can pull the gastrostomy device 100 at the connector arrangement 400. Then the gastrostomy device 100 can be secured with an external retaining element 620. The external retaining element 620 is slidably arranged on the tube 200 but withstands a certain pulling or pushing force due to friction between the external retaining element 620 and an outer surface of the tube 200.

In order to facilitate such pulling, the tube 200 includes indication elements 240. Such indication elements 240 can be disposed circumferentially and/or along a longitudinal direction of the tube 200. The indication elements 240 can have an arbitrarily chosen form. For instance, some of the indication elements 240 are continually provided along a longitudinal direction of the tube 200 (not shown in FIG. 1A) or can be arranged at equal intervals along a longitudinal direction of the tube 200 as illustrated in FIG. 1A. Alternatively, the indication elements 240 can be arranged at logarithmic intervals in the longitudinal direction of the tube 200, where the distances between two adjacent indication elements 240 becomes smaller the closer they are located to the distal end tip 210 or to the retaining element 300. Furthermore, the indication elements 240 can also be provided with numerals, in order to indicate a distance to the distal end tip 210 or the distance to the retaining element 300. For example, the numerals can indicate such distance in centimeters or millimeters.

Furthermore, the tube 200 further includes a second lumen, i.e. a gastric lumen, extending in a longitudinal direction of the tube 200. The gastric lumen extends from a proximal end up to a distal end tip 210 of the tube 200. The gastric lumen is configured to let nutrition and/or medication and/or gas(es) pass through. Therefore, nutrition, medication and/or gas(es) can be led into or removed from the body cavity of the patient, such as the stomach. In order to facilitate supply of nutrition, medication and/or gas(es), a fitting 500 or fitting arrangement (e.g., according to ISO 80369-3) is provided at the proximal end of the tube 200.

FIGS. 1A and 1B further illustrate an exemplary sheath 610, 615 sheathing a portion of the gastrostomy device 100. Such sheath 610, 615 can be employed to form an access sheath into the body cavity, for example, into the stomach through the abdominal wall and stomach wall. Alternatively, such sheath 610, 615 may be a protection sheath for the retaining element 300, when it is in an empty state, for example, for transportation and before and during insertion into the body cavity. In order to remove the sheath 610, 615, it can be teared apart by pulling the two illustrated handles away from each other. The sheath 610, 615 is provided with a predetermined breaking line along the longitudinal direction of the sheath 610, 615.

FIG. 2 shows a side view of a gastrostomy device 100 and of a trocar 10, each including a sheath 610, 615 sheathing a portion of the gastrostomy device and the trocar, respectively. The illustrated gastrostomy device 100 and trocar 10 can be part of a gastrostomy kit, which is provided "ready for use". The gastrostomy device 100 includes the same components as the gastrostomy device 100 of FIGS. 1A and 1B, so that the description of such components is omitted for brevity of the present disclosure.

The trocar 10 provided in the gastrostomy kit is inserted into an access sheath 615 and can be locked at a handle at the access sheath 615. The trocar 10 can then be used to puncture an opening through the abdominal wall and stomach wall of the patient by holding the trocar 10 at the knob 15 and pressing the sharp end of the trocar 10 through the abdominal wall and stomach wall. The trocar 10 can be made of stainless steel or PEEK (Polyether ether ketone) with a sharp distal pin end. When inserted, a distal end of the access sheath 615 enters the stomach of the patient. For example, the access sheath 615 can have a size of CH 10 to CH 20 (CH=Charrìere, a measuring unit for the outer diameter of tubular devices; 1 CH is approximately 0.33 mm) and may include Teflon to facilitate relative movement of the access sheath 615 and the trocar 10.

This process can be observed with a simple endoscope provided into the stomach of the patient. Since the endoscope is only used to inflate the stomach with air and to provide an image from the inside of the stomach, the smallest available endoscope can be used. For example, a small tube endoscope (having a diameter of only 4.3 mm) can be used, which may be inserted through the nose of the patient. This helps reducing the risk of moving any infectious germs from the throat and/or esophagus of the patient into the stomach and is more comfortable for the patient.

Once inserted, the trocar 10 is removed, while the access sheath 615 maintains in the body of the patient. A valve in the access sheath 615 can close when the trocar 10 is removed, in order to prevent air from escaping from the inflated stomach. For instance, the valve can be disposed in a handle of the access sheath 615. Subsequently, the gastrostomy device 100 can be inserted through the access sheath 615. As illustrated in FIG. 2, a distal end of the gastrostomy tube 200 is covered by a protection sheath 610. The protection sheath 610 can be identically constructed as the access sheath 615. However, the protection sheath 610 can be shorter than the access sheath 615. The protection sheath 610 protects the retaining element 300 provided at the distal end part of the tube 200.

In order to facilitate insertion of the gastrostomy device 100 into the patient's body cavity, the protection sheath 610 can be abutted against a proximal end of the access sheath 615. Thereby the tubular parts of the access and protection sheaths 610, 615 can be brought into alignment, so that both sheaths 610, 615 form a continuous tube. The distal end of the gastrostomy device 100, and in particular the distal end of the tube 200, is pushed through the protection sheath 610 into the access sheath 615 and further into the body cavity of the patient. This insertion can still be observed with the endoscope. By connecting the protection sheath 610 and the access sheath 615 a valve in the access sheath 615 (e.g. in the handle thereof) can be opened. Alternatively, the valve can be opened by the distal end of the tube 200 when pushed through the protection and access sheaths 610, 615.

When brought in place, the retaining element 300 is inflated. This retains the gastrostomy device in the body cavity. Then the access and protection sheaths 610, 615 can be removed from the patient and the gastrostomy device 100 by tearing them apart. Thereafter, the tube 200 can be pulled in a longitudinal direction away from the patient's body abutting the retaining element 300 to the body cavity wall (e.g., stomach wall). Then the gastrostomy device 100 is secured with an external retaining element 620. The external retaining element 620 can be a disk-like element that glides over an exterior surface of the tube 200. When pulling the gastrostomy device 100 away from the patient's body and, at the same time, pushing the external retaining element 620 along the tube 200 towards the patient's body, the abdominal wall and stomach wall are squeezed together and hold in place by both retaining elements 620, 300. In this position, a stoma is formed within two to four weeks.

FIG. 3 shows a side view of a gastrostomy device 100 including the two sheaths 610, 615 sheathing parts of the gastrostomy tube 200. In particular, FIG. 3 illustrates how the distal end 205 of the tube 200 and the retaining element 300 protrude from a distal end of the access sheath 615. This corresponds to the inserting process, where the empty retaining element 300 enters the body cavity.

The protection sheath 610 is illustrated spaced apart from the access sheath 615. However, it is to be understood, that during the insertion process, the protection sheath 610 may abut against the proximal end of the access sheath 615 forming a continuous passage for the gastrostomy tube 200.

FIGS. 4A to 4D show an enlarged distal end of a gastrostomy device 100, and in particular a distal end 205 of a gastrostomy tube 200 and a retaining element 300 sheathed by an access sheath 615 and a protection sheath 610 and further show different states of the retaining element. FIG. 4A illustrates how the access and protection sheaths 610, 615 form a continuous passage. This drawing further shows that a first portion (distal end portion) of the empty retaining element 300 protrudes from a distal end of the access sheath 615. This will take place while the access sheath 615 is provided through the abdominal wall and stomach wall of the body of the patient.

When pushed further, the entire empty retaining element 300 and the distal end tip 210 of the tube 200 will protrude from the distal end of the access sheath 615, as illustrated in FIG. 4B. In its empty state the retaining element 300 can cover the distal end tip 210 of the tube 200. Thus, the empty retaining element 300 forms a distal end of the gastrostomy device 100 during the insertion process. From the enlarged view of the distal end 205 of the tube 200 shown in FIG. 4C it is derivable that the retaining element 300 takes up space adjacent to the distal end 210 of the tube 200 in a longitudinal direction of the tube 200. This facilitates folding the retaining element 300 and providing it within the protection sheath 610. Since the distal end of the folded retaining element 300 can use the entire cross-sectional area of the protection sheath 610, kinks or other sharp folding edges of the retaining element 300 are avoided.

A surface of the retaining element 300 in its empty state has an area substantially equal to an area of the surface of the retaining element 300 when in its inflated state. In other words, the material of the retaining element 300 has almost no prolongation when being inflated. Thus, the empty retaining element 300 when being stowed requires more volume than, for example, an elastically extendable retaining element, such as the conventional retaining element made from elastic silicone.

FIG. 4D shows the distal end 205 of the tube 200, where the retaining element 300 is inflated. As illustrated in FIG. 4D, a portion 330 of the inner layer of the retaining element 300 is coupled to a portion 220 of the tube 200. Furthermore, the retaining element 300 is coupled to the tube 200 at two portions of the tube 200 spaced apart from each other, although only one portion 220 is visible in the drawing. The distal end 210 of the tube 200 protrudes from the retaining element 300. This facilitates the effusing of nutrition, medication and/or gas(es) from the distal end 210 of the tube 200.

FIG. 5A shows a cross-sectional view of a retaining element 300 in an inflated state at a distal end 205 of a gastrostomy tube 200. The retaining element 300 includes at least one tubular extension 320, 330 having a cross-section configured for coaxially surrounding the tube 200. In particular, a first tubular extension 320 surrounds a first portion 225 of the tube 200 and a second tubular extension 330 surrounds a second portion 220 of the tube 200.

The tube 200 includes a gastric lumen 230 and a retainer lumen 235 both extending in a longitudinal direction of the tube 200. Between the first portion 225 and the second portion 220 of the tube 200 an opening 250 in an outer skin of the tube 200 may be provided. This opening 250 provides for a fluid communication between the retainer lumen 235 and an interior space of the retaining element 300. Any fluid provided into the retainer lumen 235 can flow into the interior space of the retaining element 300, thereby inflating the retaining element 300.

The retaining element 300 comprises an inner layer made of polyurethane (PUR) and an outer layer made of polyamide (PA). The tubular extensions 320, 330 can be formed at least from the inner PUR-layer. A watertight connection is provided between the tubular extensions 320, 330 and the first and second portions 225, 220 of the tube 200, respectively. For example, the tubular extensions 320, 330 can be welded, adhered, shrink fitted, etc. onto the first and second portions 225, 220 of the tube 200, respectively. According to an example, at least portions 220, 225 of the tube 200 can be made of polyurethane (PUR), so that a solvent or heat bonding between the tubular extension 320, 330 (made also of PUR) with the respective portion 220, 225 of the tube 200 can be achieved easily. It is to be understood that the entire tube 200 can be made of PUR. The retaining element 300 can include an outer layer made of polyamide (PA). The outer PA-layer can extend at least partially on the at least one tubular extension 320, 330. In addition, the PA-layer can cover the entire tubular extensions 320, 330 as well as a part or all of an exterior surface of the tube 200. For instance, when the retaining element 300 is fixed to the tube 200, most parts of the gastrostomy device 100 can be dipped into a solution coating the retaining element 300 and the tube 200 with a PA-layer. Alternatively, the retaining element 300 is formed from a double layer tube consisting of PUR and PA layers and the tube 200 is also a double layer tube consisting of an inner PUR layer and an outer PA layer. In this case, the PA layer can be removed from the tube 200 at the two portions where the tubular extensions 320, 330 will be adhered, so that the PUR-layers of the tube 200 and the tubular extensions 320, 330 come into contact with each other.

FIG. 5A further shows that the tube 200 can have different cross-sections along a longitudinal axis of the tube 200. For example, with the opening 250 into the retainer lumen 235 the retainer lumen 235 can end. Therefore, the tube 200 may be formed between the opening 250 and the distal end tip 210 with a cross-section having only the gastric lumen 230. This allows a smaller outer diameter of the distal end of the tube 200, creating more space in particular in an area where the empty retaining element is disposed when folded.

Furthermore, the tube 200 may be provided with indication elements 240, such as symbols 241 or tick marks of a scale. Such symbols 241 are provided on a portion of the tube 200 facing towards the proximal end of the tube, i.e. a portion that will lie outside of the body of the patient when the gastrostomy device 100 is placed in the patient's body cavity. The indication elements 240 may be arranged circumferentially and/or in a longitudinal direction of the tube 200 at any desired distance. In a circumferential direction, the indication elements 240 can be uniformly distributed, such as three indication elements every 120° (not shown in FIG. 5A). The symbols 241 can be spaced apart from each other in the longitudinal direction of the tube 200 by a predetermined distance. For example, symbols 241 can be provided at equal intervals, such as 0.5 cm, 1 cm, 1.5 cm, or any other distance required to form a scale indicating a distance to the retaining element 300 and, in particular, a distance to the surface 340 of the retaining element 300 abutting the stomach wall. The symbols 241 may surround the tube 200 entirely (forming rings on a surface of the tube 200 as illustrated in FIG. 5A) or may be subdivided in a circumferential direction. The indication elements 240 can be printed onto the surface of the tube 200 or may be integrated into the tube wall of tube 200.

As can be derived from FIG. 5A, the retaining element 300, in an inflated state, can have a substantially ellipsoidal form. It is to be understood that the retaining element 300 does not need to have a perfectly symmetrical ellipsoidal form. For instance, the retaining element 300 may comprise one or more flat or plane surfaces 340, 345. It is particularly advantageous if a surface that will abut against the stomach wall of the patient has a flat or plane portion 340, since this provides good retaining properties. The retaining properties can be enhanced, if the flat or plane portion 340 is disposed substantially perpendicular to a longitudinal axis of the tube 200.

Alternatively, as illustrated in FIG. 5B, the flat or plane surface 340 of FIG. 5A may be bent inwardly, i.e. towards a center of the retaining element 300. This can be achieved by moving the proximal tubular extension 330 closer to the distal end of the tube 200 before adhering the proximal tubular extension 330 to the tube 200. Alternatively or additionally, the retaining element 300 may be fabricated as having a bulge that is maintained due to the form durability of the PUR- and PA-layers of the retaining element 300, where the proximal tubular extension 330 lies closer to a center of the retaining element 300. This provides additional flexibility for the gastrostomy device 100 when the retaining element 300 abuts against the wall of the body cavity, such as the stomach wall, around the stoma. Thus, the wall of the body cavity is less irritated by the proximal tubular extension 330 and/or the surface 340 of the retaining element 300.

Additionally or alternatively, the retaining element 300 can be provided with a bulgy form on the opposite (distal) side, i.e. at surface 345. Likewise, the distal tubular extension 320 may be adhered to the tube 200 resulting in the bulgy form of the retaining element 300 and/or the retaining element 300 may be fabricated with such bulgy form.

Also additionally or alternatively, the retaining element 300 can be provided with a flat or plane surface 345 on its distal side and the distal tubular extension 320 is brought closer to the proximal end of the tube 200 before adhering the distal tubular extension 320 to the tube 200. For instance, the flat or plane surface 345 can protrude further to a distal side of the gastrostomy device 100 than the distal end tip 210 of the tube 200. Such form of the retaining element 300 is illustrated in FIG. 5C. This allows providing the distal end tip 210 closer to the center of the retaining element 300. This form of the retaining element 300 and, in particular, the surface 345 of the inflated retaining element 300 then facilitates keeping the distal end tip 210 away from a corresponding wall of the body cavity (otherwise pricking into the wall of the body cavity), such as the stomach wall. Thus, the wall of the body cavity on the distal side of the retaining element 300 will not be irritated (or less irritated)

by the tube 200 (particularly its distal end tip 210) and/or the surface 345 of the retaining element 300.

It is to be understood that distal side surface 345 of the retaining element 300 is not limited to the form illustrated in FIG. 5C. The flat or plane surface 345 can instead be flush with the distal end tip 210 of the tube 200. Furthermore, it is also understood that the proximal side (surface 340) of the retaining element 300 can be formed corresponding to the distal side (surface 345) of the retaining element 300.

FIGS. 6A and 6B show cross-sections of gastrostomy tubes 200 of sizes CH10 and CH14, respectively. According to a first example shown in FIG. 6A, an outer diameter of the tube 200 can be approximately 3 mm and an inner diameter can be approximately 2 mm.

The tube wall 245 thus formed creates a gastric lumen 230. Within the tube wall 245 can be a retainer lumen 235. Both lumens 230, 235 extend in a longitudinal direction of the tube 200, wherein the gastric lumen 230 extends to a distal end tip 210 of the tube 200 and the retainer lumen 235 is in fluid communication with an interior space of the retaining element 300. Such fluid communication can be achieved by an opening (not shown in FIG. 6A) through the tube wall 245 into the retainer lumen 235 (from an exterior side of the tube 200). The retainer lumen 235 can have a cross-section forming an ellipse. Such ellipse may have a minor axis that aligns with a radially direction of a cross-section of the tube 200, as shown in FIG. 6A. The minor axis of the ellipse may have a length of approximately 0.4 mm, and a major axis of the ellipse may have a length of approximately 0.6 mm. The center of the ellipse may be about 1.1 mm from the center of the cross-section of the tube 200.

Due to the retainer lumen 235 the cross-section of the gastric lumen 230 has an indent. This indent may be formed by two curved sections moving towards the center of the tube 200, each having a radius of about 0.2 mm and an intermediate section with an opposite curvature with a radius of approximately 0.45 mm. This intermediate section can be substantially parallel to the corresponding part of the ellipse of the retainer lumen 235. Therefore, the indent into the gastric lumen 230, i.e. the interior surface of the tube wall 245 at the most indenting position, may be spaced apart from the center of the tube 200 by approximately 0.7 mm.

Furthermore, integrated into the tube wall 245 may be indication elements 240. For example, FIG. 6A depicts indication elements 240 in the form of markers 242, which are arranged in a circumferential direction. The markers 242 can be uniformly distributed, such as three markers 242 every 120°. The markers 242 can have an approximately rectangular or elliptical cross-section having dimensions of approximately 0.5 mm and 0.25 mm. The distance between a marker 242 and an exterior surface of the tube wall 245 may be about 0.08 mm, while a distance between the marker 242 and an interior surface of the tube wall 245 (the surface of the gastric lumen 230) may be about 0.04 mm. The markers 242 may extend over the entire length of the tube 200 (in a longitudinal direction of the tube 200).

According to a second example shown in FIG. 6B, an outer diameter of the (CH14) tube 200 can be approximately 4.2 mm and an inner diameter of approximately 3 mm.

The tube wall 245 thus formed creates a gastric lumen 230. Within the tube wall 245 can be a retainer lumen 235. The retainer lumen 235 can have a cross-section forming an ellipse. Such ellipse may have a minor axis that aligns with a radially direction of a cross-section of the tube 200, as shown in FIG. 6B. The minor axis of the ellipse may have a length of approximately 0.6 mm, and a major axis of the ellipse may have a length of approximately 0.8 mm. The center of the ellipse may be about 1.45 mm from the center of the cross-section of the tube 200.

Due to the retainer lumen 235 the cross-section of the gastric lumen 230 has an indent. This indent may be formed by two curved sections moving towards the center of the tube 200, each having a radius of about 0.3 mm and an intermediate section with an opposite curvature of a radius of approximately 0.65 mm being substantially parallel to the corresponding part of the ellipse of the retainer lumen 235. Therefore, the indent into the gastric lumen 230 may be closer to the center of the tube 200 than the remaining interior surface of the tube wall 245.

Furthermore, integrated into the tube wall 245 may be indication elements 240. For example, FIG. 6B depicts indication elements 240 in the form of markers 242 may be arranged in a circumferential direction. The markers 242 can be uniformly distributed, such as three markers 242 every 120°. The markers 242 can have an approximately rectangular or elliptical cross-section having dimensions of approximately 0.8 mm and 0.3 mm. The distance between a marker 242 and an exterior surface of the tube wall 245 may be about 0.08 mm, while a distance between the marker 242 and an interior surface of the tube wall 245 (the surface of the gastric lumen 230) may be about 0.04 mm. The markers 242 may extend over the entire length of the tube 200 (in a longitudinal direction of the tube 200).

Alternatively or additionally to markers 242 integrated into the tube wall 245, symbols 241 (not shown in FIGS. 6A and 6B) can also be printed onto an exterior surface of the tube wall 245.

FIGS. 7A and 7B show a perspective view and a side view of a connector arrangement 400 provided at a proximal part of the tube, respectively, and illustrate different details of the connector arrangement 400. Specifically, FIG. 7A illustrates the outlines of a casing for an indicator 410. The indicator 410 can be in fluid communication with the retainer lumen 235. For clarity reasons of this drawing the detailed components of the indicator were omitted. The indicator can be couple to a fitting 411, which is in fluid communication with the retainer lumen 235. The indicator 410 is configured for indicating a pressure of the retaining element 300 continuously within a range from a pressure corresponding to an empty retaining element 300 to an optimal pressure for the inflated retaining element 300.

As illustrated in FIG. 7B, the indicator 410 can have a scale 420 provided on or in the housing of the indicator 410 in a manner, so that it is visible from the outside of the indicator 410. The scale 420 comprises at least two sections 421, 422. A first section 421 can indicate that the pressure in the retaining element 300 corresponds to the empty or an insufficiently inflated retaining element 300, and a second section 422 indicates that the pressure in the retaining element is in an optimal pressure range for the inflated retaining element 300. The first section 421 can be provided with a color, pattern or other means to highlight that the pressure in the retaining element 300 corresponds to an empty retaining element 300 or is a critically low pressure for the retaining element 300. For instance, a critically low pressure would be a pressure of an insufficiently inflated retaining element 300, providing a risk that the retaining element 300 cannot sufficiently retain the gastrostomy device 100 and that the gastrostomy tube 200 may move out of the stoma. Such critically low pressure could be indicated by a red colored section 421. The second section 422 corresponds to a section of the scale 420 indicating an optimal pressure range. The optimal pressure range corresponds to a pressure in the retaining element 300 when the retaining element 300 is inflated, but not pressure-loaded, i.e. no significant pressure force acts on to the retaining element 300 from an outside thereof. As an example only, the pressure within the filled/inflated retaining element 300 can be between approximately 35 mbar to 75 mbar. Therefore, the second section 422 may be provided with a color, pattern or other means that indicates the optimal pressure range, such as a green color.

According to a further example, the indicator 410 can be configured for further continuously indicating a pressure in the retaining element 300 corresponding to a pressure-loaded pressure range of the retaining element 300, i.e. of a retaining element 300 onto which pressure forces act from an outside thereof. For instance, a force may act onto the retaining element 300 when the gastrostomy tube 200 is pulled and the retaining element 300 abuts against the stomach wall. Thus, the pressure-loaded range can also be referred to as a critically high pressure range. For instance, if the gastrostomy tube 200 is pulled and the retaining element 300 abuts against the stomach wall, the pressure within the retaining element 300 may increase to approximately 100 mbar to 150 mbar.

The scale 420 of the indicator 410 can comprise a third section 423 indicating the pressure-loaded range. For example, the third section 423 can be provided in a color, pattern or other means to highlight that the pressure in the retaining element 300 corresponds to (falls into) the pressure-loaded range. In order to distinguish the third section 423 from the first section 421 (both indicating a critical pressure), a different color, pattern or other means could be used for the two sections 421, 423. For instance, the third section 423 may be colored in orange, blue or yellow.

FIGS. 7A and 7B illustrate the connector arrangement 400 exemplarily as a Y-connector 470. Thus, the connector arrangement 400 includes a first branch 471 and a second branch 472 of the Y-connector 470. At a proximal end of the first branch 470 may be a connector 460 configured for receiving a filling means (not shown), such as a syringe. The connector 460 can be in fluid communication with the retainer lumen 235 of the tube 200 at the proximal part of the tube 200. This allows filling a fluid from a filling means through the retainer volume 235 into the retaining element 300 and also removing the fluid from the retaining element 300 the opposite way.

An optional protection cap (not shown) can be applied to the connector 460 after the fluid has been filled into the retaining element 300. This avoids a possible misconnection of the connector 460 with a further lumen or syringe delivering nutrition, medication or the like into the retainer lumen 235 and the retaining element 300.

In the illustrated form the first branch 471 of the Y-connector 470 also forms a pull handle 450 connected to the tube 200 in a force-fitting manner. Thus, the connector 460 is integrally formed with the pull handle 450. The pull handle 450 can be configured for pulling the tube 200. This provides the user of the gastrostomy device 100 a means for pulling the retaining element 300 to abut against the stomach wall of the patient and to affix the gastrostomy device 100 with the second retaining element 620.

Alternatively, the pull handle 450 can be formed separately from the connector arrangement 400. For instance, the pull handle 450 can be coupled to the tube 200 in a force-fitting manner in front of or behind the connector arrangement 400 when contemplating the tube 200 in a longitudinal direction of the tube 200.

FIGS. 8A and 8B show sectional side views of the connector arrangement 400 including various exemplary details. For instance, the fluid communication between the connector 460 and the retainer lumen 235 may be achieved by an opening 260 in the outer tube wall 245 and into the retainer lumen 235. The opening 260 opens out into a tubular component 462 extending between the opening 260 and the connector 460.

Furthermore, as illustrated in FIG. 8A, the connector 460 can include a valve 465 configured for blocking and de-blocking the fluid communication to the retainer lumen 235. The valve 465 as illustrated will be pushed towards opening 260 when a filling means (not shown) is inserted into connector 460. This provides an opening at gap 466 of the connector 460. While the filling means will be sealed at an inner surface of the connector, a watertight connection can be achieved between the filling means and connector 460 to allow a fluid to flow from the filling means to the retainer volume 235 and back. The valve 465 is provided with means 467 pressing the valve 465 towards connector 460 for deblocking the fluid communication between the connector 460 and the retainer lumen 235. For instance, means 467 can be any pre-loaded spring, such as an elastically deformable element made from silicone, pressing the valve 465 towards the gap 466 of connector 460. Alternatively, the valve 465 may also extend through tubular component 462 and block and deblock opening 260 instead of or additionally to gap 466 of the connector 460.

As illustrated in FIGS. 8A and 8B, fitting 411 is also in fluid communication with the retainer lumen 235. For instance, a tubular component 412 may be in fluid communication with the tubular component 462 of the connector 460.

According to a first exemplary indicator 410 illustrated in FIG. 8A, attached to the fitting 411 is a hollow member 430. The hollow member 430 may include a corresponding fitting for detachably connecting the hollow member 430. The hollow member 430 of the indicator 410 is in fluid communication with the retainer lumen 235. For example, the fluid communication can be achieved via tubular components 462 and 412. The hollow member 430 can be configured to receive and hold an amount of a fluid from the retainer lumen 235 (i.e., from the tubular component 462) in proportion to the pressure in the retaining element 300 (and hence in the retainer lumen 235, tubular component 462 and tubular component 412). The hollow member 430 may have a neutral position as illustrated in FIG. 8A, where the hollow member 430 has a curved form. In this form the hollow member 430 is in an empty state. When a pressure of the fluid in the retaining element 300 (and hence in the retainer lumen 235, tubular component 462 and tubular component 412) increases, the fluid flows into hollow member 430. The hollow member 430 is capable of receiving and holding a certain amount of fluid, which leads to an increasing filling/inflation of the hollow member 430 from its end connected to fitting 411 towards its opposite (free) end.

Furthermore, the hollow member 430 is configured to straighten when receiving the fluid. This straightening begins at or close to the fitting 411 and grows towards the free end of the hollow member 430 depending on the pressure of the fluid entering the hollow member 430 in a longitudinal direction thereof. For example, the hollow member 430 may include at least one shell component that is pre-stressed, so that in a cross-sectional view of the hollow member 430 the at least one pre-stressed shell component presses onto another cross-sectional component(s) (portion(s)) of the hollow member 430. Thus, if the fluid pressure increases, the fluid presses the pre-stressed shell component away from the remaining (cross-sectional) component(s) of the hollow member 430, thereby partially and increasingly inflating the hollow member 430 in a longitudinal direction thereof. This inflation also straightens the hollow member 430, since the fluid in the (already) inflated parts of the hollow member 430 inhibits the curved form of the hollow member 430. Thus, proportional to the pressure of the fluid, a part of the hollow member 430 straightens. For instance, the hollow member 430 can be made of polyurethane (PUR or PU) or alternatively from silicone.

When contemplating FIGS. 7B and 8A it becomes apparent that the hollow member 430 when straightening due to an increased pressure of the fluid will move in such a manner that at least a part of the hollow member 430 is visible through a window 480. Thus, in a very simple to implement manner a visual indication of the pressure in the retaining element 300 is given to a user of the gastrostomy device 100.

The hollow member 430 may also have a visual indicator 435 visible from an outside of the indicator 410. Thus, when the hollow member 430 is inflated by the fluid, e.g. due to an increasing pressure of the fluid in the retainer lumen 235, the visual indicator 435 will also move on a spline or an elliptical or circular path. If the housing of the indicator 410 is provided with a window or opening 480 approximately having the form of the movement of the visual indicator 435, the visual indicator 435 of the hollow member 430 indicates a pressure in the retaining element 300. Such window can be arranged within or near the sections 421-423 of the scale 420.

According to a further example illustrated in FIG. 8B, the indicator 410 may comprise a piston 440 movably disposed inside the hollow member 430. An outer surface of the piston 440 can sealingly fit to an inner surface of the hollow member 430. The piston 440 can glide inside the hollow member 430. Thus, the piston 430 can move due to a pressure change inside the retainer lumen 235. A return member 445 configured for returning the piston 440 is also provided in the indicator 410. The return member 445 returns the piston 440 to a neutral position inside the hollow member 430. For example, the return member 445 can be a spring or can be a gas that is sealed within the hollow member 430 by the piston 440. The neutral position can correspond to a pressure in the retainer lumen 235 when the inflatable retaining element 300 is in an empty state. Thus, in case of an increasing pressure in the retaining element 300 and retainer lumen 235 the piston 440 will be pressed against the force of the return member 445 and will move towards the free end of the hollow member 430.

The indicator 410, according to the example illustrated in FIG. 8B, can also include a visual indicator 446 visible from an outside of the indicator 410. The visual indicator 446 is coupled to the piston 440, for example, with a magnetic coupling. The visual indicator 446 can be visible from an outside of the indicator 410 through a window 480. Alternatively, the visual indicator 446 can be integrally formed with the piston 440. In this case, the hollow member 430 has to be transparent at least at the portion facing the window 480, so that the visual indicator 446 is visible from the outside.

According to any example illustrated in and described with respect to FIGS. 8A and 8B, the window 480 in a casing of the indicator 400 can be arranged with respect to the scale 420, and in particular over all sections 421, 422, 423 of the scale 420. This provides for the visually indicating the pressure in the retaining element 300 at indicator 410 over the entire pressure range, from an empty retaining element 300 to a pressure-loaded retaining element 300.

Referring back to FIG. 8A, a further detail of the gastrostomy device 100 is shown. Specifically, the tube 200 can pass through the Y-connector 470 and extends from the second branch 472 of the Y-connector 470. At an end of the tube 200 spaced apart from the indicator arrangement 400 can be a fitting 500 (see FIGS. 1A and 1B) for connecting any device to the gastric lumen 230 and providing a fluid communication therewith.

Alternatively, as illustrated in FIG. 8B, the second branch 472 of the Y-connector 470 includes a fitting 500. Thus, any device can be connected to the gastric lumen 230 having a fluid communication directly at the connector arrangement 400. This provides for a more compact gastrostomy device 100.

The above described aspects, variants and implementations of a gastrostomy device do not limit the present disclosure. Any details described with respect to one of the illustrated gastrostomy devices (aspects, variants and implementations) may also be implemented or applied to another one of the described gastrostomy devices (aspects, variants and implementations).

The invention claimed is:

1. A gastrostomy device, comprising:
   a gastrostomy tube having a retainer lumen extending between a proximal part and a distal part of the tube;
   an inflatable retaining element coupled to the tube at the distal part, wherein an interior space of the retaining element is in fluid communication with the retainer lumen;
   and an indicator being in fluid communication with the retainer lumen at the proximal part of the tube, wherein the indicator is configured for indicating a pressure in the retaining element continuously within a range from a pressure corresponding to an empty retaining element to an optimal pressure for the inflated retaining element,
   characterized in that the indicator comprises:
   a hollow member being in fluid communication with the retainer lumen at the proximal part of the tube, wherein the hollow member is configured to receive and hold an amount of a fluid from the retainer lumen in proportion to the pressure in the retainer element,
   wherein the hollow member has a free end and is configured to have a curved form, when in an empty state, and to straighten, when receiving the fluid, wherein the free end of the hollow member moves along a spline or an elliptical or circular path,
   wherein the indicator has a scale comprising two sections, wherein a first section indicates that the pressure in the retaining element corresponds to the empty or an insufficiently inflated retaining element, and a second section indicates that the pressure in the retaining element is in an optimal pressure range for the inflated retaining element,
   and wherein the hollow member has a visual indicator visible from an outside of the indicator.

2. The gastrostomy device according to claim 1, wherein the indicator is configured for further continuously indicating a pressure in the retaining element corresponding to a pressure-loaded pressure range of a pressure-loaded retaining element.

3. The gastrostomy device according to claim 2, wherein the scale of the indicator comprises a third section indicating the pressure-loaded range.

4. The gastrostomy device according to claim 1, wherein the indicator comprises a housing with a transparent window, wherein the visual indicator is visible from the outside of the indicator through the window.

5. The gastrostomy device according to claim 1, further comprising:
a fitting configured for detachably connecting the hollow member to a lumen being in fluid communication with the retainer lumen.

6. The gastrostomy device according to claim 1, further comprising:
a pull handle connected to the tube in a force-fitting manner, wherein the pull handle is configured for pulling the tube.

7. The gastrostomy device according to claim 1, further comprising:
a connector configured for receiving a filling means and being in fluid communication with the retainer lumen of the tube at the proximal part, wherein the connector includes a value configured for blocking and deblocking the fluid communication to the retainer lumen.

8. The gastrostomy device according to claim 7, wherein the connector is integrally formed with the pull handle.

9. The gastrostomy device according to claim 8, wherein the connector forms part of a first branch of a Y-connector.

10. The gastrostomy device according to claim 9, wherein a second branch of the Y-connector includes a fitting, or
wherein the tube passes through the Y-connector and extends from the second branch of the Y-connector.

11. The gastrostomy device according to claim 1, wherein the tube further comprises a gastric lumen extending at least between the proximal part and the distal part of the tube, wherein the gastric lumen is configured to let nutrition and/or medication and/or gases pass through.

12. The gastrostomy device according to claim 11, wherein the gastric lumen extends to a distal end tip of the tube.

13. The gastrostomy device according to claim 11, wherein the retainer lumen has a cross-section forming an ellipse, wherein a minor axis of the ellipse aligns with a radially direction of a cross-section of the tube.

* * * * *